United States Patent
Villazón-Terrazas et al.

(10) Patent No.: US 11,610,678 B2
(45) Date of Patent: Mar. 21, 2023

(54) MEDICAL DIAGNOSTIC AID AND METHOD

(71) Applicant: FUJITSU LIMITED, Kawasaki (JP)

(72) Inventors: Boris Villazón-Terrazas, Madrid (ES); Nuria Garcia Santa, Madrid (ES)

(73) Assignee: FUJITSU LIMITED, Kawasaki (JP)

(*) Notice: Subject to any disclaimer, the term of this patent is extended or adjusted under 35 U.S.C. 154(b) by 333 days.

(21) Appl. No.: 16/591,623

(22) Filed: Oct. 3, 2019

(65) Prior Publication Data
US 2020/0118682 A1 Apr. 16, 2020

(30) Foreign Application Priority Data

Oct. 12, 2018 (EP) .................................. 18200164

(51) Int. Cl.
*G16H 50/20* (2018.01)
*G16H 10/60* (2018.01)
*G06N 20/00* (2019.01)

(52) U.S. Cl.
CPC ............. *G16H 50/20* (2018.01); *G06N 20/00* (2019.01); *G16H 10/60* (2018.01)

(58) Field of Classification Search
CPC ........ G16H 50/20; G16H 10/60; G16H 50/70; G06N 20/00
See application file for complete search history.

(56) References Cited

U.S. PATENT DOCUMENTS

| 7,379,946 B2 | 5/2008 | Carus et al. |
| 2008/0004505 A1 | 1/2008 | Kapit et al. |
| 2008/0288292 A1 | 11/2008 | Bi et al. |
| 2013/0041685 A1 | 2/2013 | Yegnanarayanan |
| 2014/0046696 A1 | 2/2014 | Higgins et al. |
| 2016/0048638 A1 | 2/2016 | Romanowski |
| 2016/0048655 A1 | 2/2016 | Maitra et al. |
| 2016/0063887 A1 | 3/2016 | Petritaj |
| 2016/0132648 A1 | 5/2016 | Shah et al. |

(Continued)

OTHER PUBLICATIONS

Garren Gaut, et al. "Content Coding of Psychotherapy Transcripts Using Labeled Topic Models", IEEE Journal of Biomedical and Health Informatics, vol. 21, p. 476-487 (2017) (Year: 2017).*

(Continued)

*Primary Examiner* — Gregory D. Moseley
(74) *Attorney, Agent, or Firm* — Xsensus LLP

(57) ABSTRACT

Methods for assisting medical personnel in performing a diagnosis, diagnostic aids and computer readable media. The method initialisation step comprises: receiving a plurality of input medical texts tagged with potential medical codes; curating and validating the plurality of input medical texts to output a subset of medical texts that are validated and tagged with medical codes; and using the subset of tagged and validated medical texts to model the associations between the medical texts and the medical codes, and generating a medical text learning model based on the associations. The method diagnostic step comprises: inputting a specimen text relating to a patient into the medical text learning model; processing the specimen text using the medical text learning model; identifying suggested medical codes based on the specimen text; and outputting diagnoses, symptoms and treatments linked to the suggested medical codes for assisting medical personnel in providing a diagnosis for the patient.

17 Claims, 8 Drawing Sheets

(56) References Cited

U.S. PATENT DOCUMENTS

2017/0109485 A1    4/2017    Dadey
2019/0279767 A1*    9/2019    Bates ..................... G16H 15/00
2020/0045119 A1*    2/2020    Weldemariam ......... H04L 67/22

OTHER PUBLICATIONS

Shaodian Zhang, et al. "Longitudinal analysis of discussion topics in an online breast cancer community using convolutional neural networks" Journal of Biomedical Informatics, vol. 69, p. 1-9 (2017) (Year: 2017).*

Shaodian Zhang, et al, "Longitudinal analysis of discussion topics in an online breast cancer community using convolutional neural networks" Journal of Biomedical Informatics, vol. 69, p. 1-9 (Year: 2017).*

Elena Tutubalina, et al., "Exploring convolutional neural networks and topic models for user profiling from drug reviews", Multimedia Tools Appl vol. 77, p. 4791-4809 (Year: 2018).*

Daniel Ramage et al: "Labeled LDA: a supervised topic model for credit attribution in multi-labeled corpora", Proceedings of The 2009 Conference on Empirical Methods in Natural Language Processing; Aug. 6, 2009 (Aug. 6, 2009), pp. 248-256, XP002689659.

Communication pursuant to Article 94(3) EPC dated Mar. 11, 2021, in corresponding European Patent Application No. 18 200 164.4.

Khare et al., "Scaling drug indication curation through crowdsourcing", Database, Article ID bav016, vol. 2015, pp. 1-10.

Mikolov et al., "Efficient Estimation of Word Representations in Vector Space", pp. 1-12, Sep. 7, 2013.

Extended European Search Report dated Apr. 29, 2019 for 18200164.4 filed on Oct. 12, 2018.

* cited by examiner

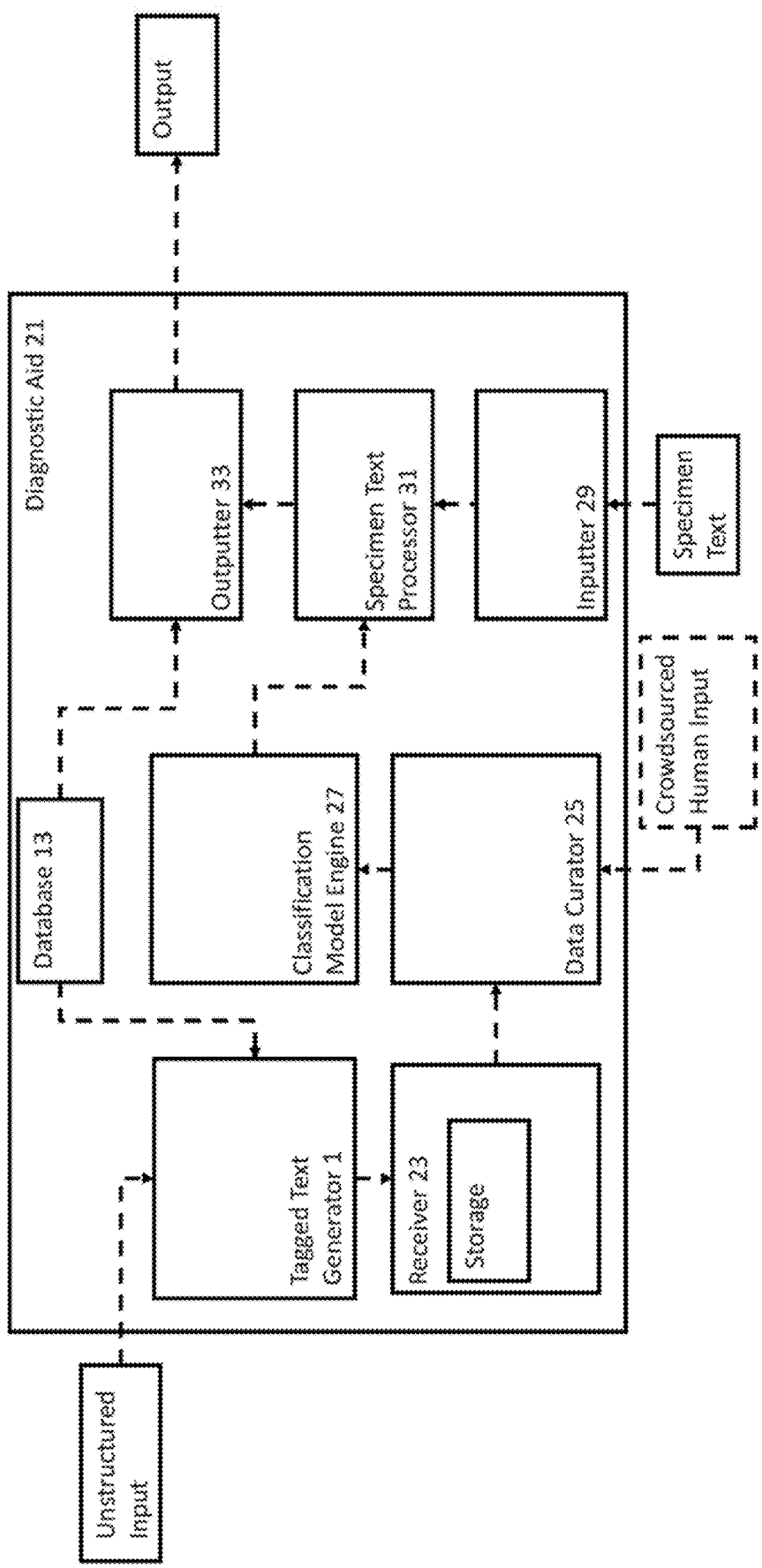

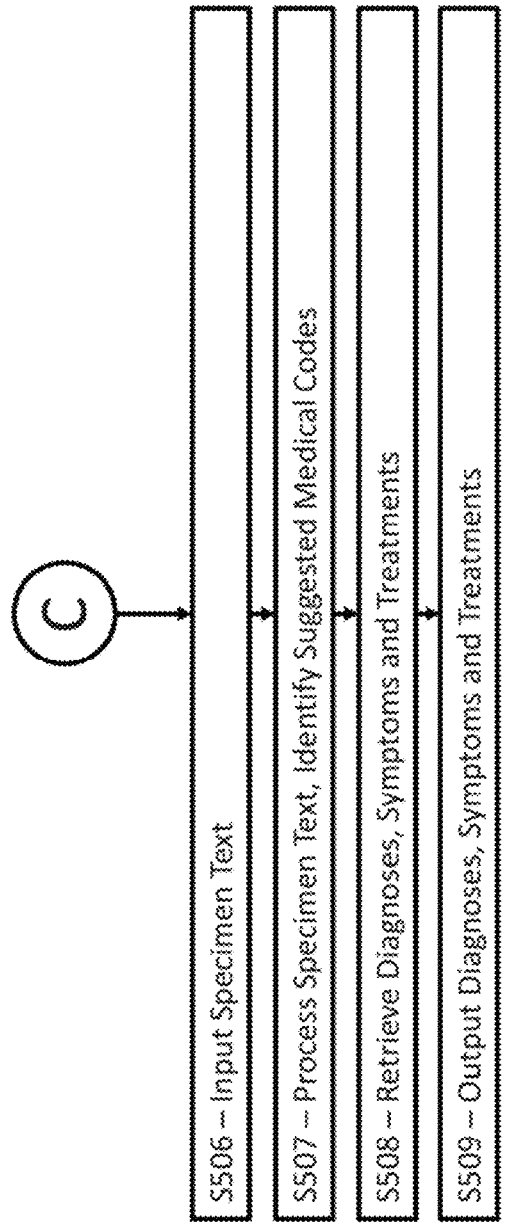

MEDICAL DIAGNOSTIC AID AND METHOD

The present application claims priority to EP 18200164.4, filed Oct. 12, 2018, the entire contents of which are incorporated herein by reference.

The invention relates to a medical diagnostic aid and method for assisting medical personnel in performing a diagnosis. Also disclosed is a computer program code which, when executed by a computer, causes the computer to perform the method, and a non-transitory computer readable medium comprising the computer program.

Natural Language Processing (NLP) is a way for computers to analyse, understand, and derive meaning from natural human language (as opposed to machine language, such as computer code). NLP is a very important field of research focused in the combination of formal theories, statistical data, machine learning and highlighting the use of semantics and contextualisation to extract the meaning of the texts.

One area of human activity to which NLP is particularly well suited is medical practice and research. The clinical and research medical community creates, manages and uses a wide variety of semi-structured and unstructured textual documents. As such, NLP and Text Mining have become crucial tools in healthcare and the life sciences. The patients' medication histories and their responses during, for example, consultations with medical practitioners may be used to inform future medical treatment. However, currently this information is typically recorded in non-standardised forms, which may increase the difficulty in subsequently retrieving useful information from records of past consultations.

As more and more information is available in the Electronic Health Records (EHRs) in the form of free-text narrative, there is a need for automated tools, which may process and understand such texts. Currently doctors and medical professionals spend a lot of time on processing free text medical notes. Due to time pressures, it is common for medical professionals not to be able to dedicate sufficient time to processing notes. Another important input in healthcare is the doctor-patient conversation as diagnostic assessment, which is key to evaluate the issues and needs of a patient. Again, it is common for recording of the interaction between doctor and patient to be incompletely documented, which may negatively impact upon the treatment received by patients.

It is desirable to provide an automated or semi-automated system capable of processing large volumes of unstructured and semi-structured clinical content and deriving concepts, structure, and relationships from it. Automatic mapping of key concepts from clinical notes to a terminology is an important task to achieve for extraction of the clinical information locked in clinical notes and patient reports. There are potential benefits from such a system both on an individual patient level, and on a general practice level.

An aspect of an embodiment provides a method for assisting a medical professional in performing a diagnosis, the method comprising an initialisation step and a diagnostic step, wherein the initialisation step comprises: receiving a plurality of input medical texts tagged with potential medical codes; curating and validating the plurality of input medical texts to output a subset of medical texts that are validated and tagged with medical codes; and using the subset of tagged and validated medical texts to model the associations between the medical texts and the medical codes and generating a medical text learning model based on the associations and wherein the diagnostic step comprises: inputting a specimen text relating to a patient into the medical text learning model; processing the specimen text using the medical text learning model; identifying suggested medical codes based on the specimen text; and outputting diagnoses, symptoms and treatments linked to the suggested medical codes for assisting medical personnel in providing a diagnosis for the patient. The method may automate at least some aspects of the analysis of unstructured data or information inputs (hereinafter referred simply as "unstructured input(s)," and may therefore save time and effort for the medical practitioner, and also provide the medical practitioner with information which may not otherwise have been discovered by the medical practitioner. Further, the curation and verification of the plurality of input medical texts tagged with potential medical codes prior to the generation of the medical text learning model increases the accuracy of the dataset used to generate the model, and thereby increases the accuracy of the diagnoses, symptoms and treatments provided using the suggested medical codes from the model.

The curation and validation of the plurality of input medical texts may comprise selecting the subset of medical texts based on at least one of: the number of potential medical codes associated with text; the language text is written in; and the length of text. In this way the medical texts may be filtered both to save curation and validation time and to improve the quality of the information used to form the model.

The method of any preceding claim, wherein the curation and validation involves input from medical personnel. Medical personnel may effectively curate and validate tagged medical texts using relevant knowledge.

The curation and validation may comprise at least an initial stage and a final stage, wherein experienced medical personnel are involved in the final stage. The use of an initial and final stage increases the chances of errors being detected, and also efficiently utilises personnel time. Further, experienced medical personnel may select inexperienced medical personnel for involvement in the initial stage, to better utilise human resources.

The associations between the medical texts and the medical codes for the tagged and validated medical texts may be modelled using a Labelled Latent Dirichlet Allocation topic model, and the medical text learning model may use a convolutional neural network. In this way, the medical text learning model may be accurately formed and trained.

The plurality of input medical texts may be natural language texts. Further, the natural language texts may be notes relating to a patient consultation. By using natural language texts the burden on the original creators of the input texts is reduced.

The method may further comprise generating the plurality of input texts tagged with potential medical codes by: receiving an unstructured input; splitting the unstructured input into a plurality of logical components, and detecting medical terms in the plurality of logical components; receiving a medical classification hierarchy of medical standard codes in the form of a knowledge graph, and semantically annotating the knowledge graph with synonyms of medical terms used in the medical standard codes; analysing the medical terms detected in the plurality of logical components by the text analyser and parser, generating a list of potential matching medical standard codes for each of the medical terms, comparing the lists of potential matching medical standard codes, and outputting top matching medical standard codes based on the comparison; and inputting the unstructured input tagged with the top matching medical standard codes as one of the plurality of input medical texts. In this way, a large number of tagged input medical texts may potentially be quickly and efficiently generated, before being curated and validated then used to create the model.

The step of inputting of the specimen text may further comprise accessing a medical record linked to a patient that is the subject of the specimen text, and the outputting diagnoses, symptoms and treatments linked to the suggested medical codes for assisting medical personnel in providing a diagnosis for the patient further comprises outputting the medical record. In this way, historical medical data for the patient may be retrieved and the accuracy of the diagnoses, symptoms and treatments may be improved. Further, the medical record may then be brought up to date with the output diagnoses, symptoms and treatments.

An aspect of an embodiment provides a medical diagnostic aid for assisting a medical professional in performing a diagnosis, the diagnostic aid comprising: a first receiver configured to receive a plurality of input medical texts tagged with potential medical codes; a data curator configured to curate and validate the plurality of input medical texts, and to output a subset of medical texts that are validated and tagged with medical codes; a classification model engine configured to use the subset of tagged and validated medical texts to model the associations between the medical texts and the medical codes, and to generate a medical text learning model based on the associations; an inputter configured to input a specimen text relating to a patient into the medical text learning model; a specimen text processor configured to process the specimen text using the medical text learning model, and identify suggested medical codes based on the specimen text; and an outputter configured to output diagnoses, symptoms and treatments linked to the suggested medical codes for assisting medical personnel in providing a diagnosis for the patient. The medical diagnostic aid may provide similar advantages to those discussed above in the context of the model.

The medical diagnostic aid may further comprise: a second receiver configured to receive an unstructured input; an analyser and parser configured to split the unstructured input into a plurality of logical components, and to detect medical terms in the plurality of logical components; a mapping engine configured to receive a medical classification hierarchy of medical standard codes in the form of a knowledge graph, and semantically annotate the knowledge graph with synonyms of medical terms used in the medical standard codes; an automatic coding solver configured to analyse the medical terms detected in the plurality of logical components by the text analyser and parser, to generate a list of potential matching medical standard codes for each of the medical terms, to compare the lists of potential matching medical standard codes, and to output top matching medical standard codes based on the comparison; an enrichment engine configured to enrich the unstructured input with the top matching medical standard codes, and to output the unstructured input tagged with the top matching medical standard codes as one of the plurality of input medical texts received by the first receiver. In this way, the tagged input medical texts may be quickly and efficiently generated.

An aspect of an embodiment provides a computer readable medium comprising code which, when executed by a computer, causes the computer to execute the method. Use of a code provides a convenient way to implement the method.

DESCRIPTION OF FIGURES

The invention is described, by way of example only, with reference to the following Figures, in which:

FIG. 4 is a schematic diagram of a diagnostic aid in accordance with an aspect of an embodiment.

FIGS. 5A and 5B are a flowchart of a method for assisting a medical professional in performing a diagnosis.

DETAILED DESCRIPTION

In an aspect of an embodiment, the receiver of the medical diagnostic aid 21 receives a plurality of input medical texts tagged with potential codes. The input medical texts can comprise various types of medical texts, such as diagnostic test results, prescription notes, and so on. However, typically the medical texts are audio or written records of patient consultations or clinical notes. The inputs are usually unstructured, that is, no specific template is followed. The inputs are tagged with potential codes, which may be taken from a suitable medical classification scheme. Diagnosis codes track diseases and other health conditions. Procedure codes track interventions performed. These diagnosis and procedure codes may be used by health care providers, government health programs, private health insurance companies, workers' compensation carriers and others for a variety of applications in medicine, public health and medical informatics. Any suitable Medical Classification scheme may be used; an example of a suitable scheme is the World Health Organisation (WHO) International Statistical Classification of Diseases and Related Health Problems (ICD) scheme, for which the $10^{th}$ revision (ICD-10) is currently in active use (see http://apps.who.int/classifications/icd10/browse/2016/en for an online version of ICD-10, active as of 9 Oct. 2018). Various derived schemes, such as the International Classification of Diseases for Oncology, third edition (ICD-O-3) may also be utilised (see http://codes.iarc.fr/usingicdo.php for an online version of ICD-O-3, active as of 9 Oct. 2018). The ICD is a health care classification system that provides a system of diagnostic codes for classifying diseases, including nuanced classifications of a wide variety of signs, symptoms, abnormal findings, complaints, social circumstances, and external causes of injury or disease.

The medical texts tagged with potential medical codes may be obtained in various ways, for example, provided by medical personnel tagging consultation notes. However, requiring extensive human input when applying the medical codes may generate a substantial labour burden. As such, a preferred way of obtaining the medical texts tagged with potential codes to be input into the receiver 23 of the diagnostic aid 21 is using a substantially automated system. Accordingly, some aspects of embodiments are configured to receive unstructured inputs and generate tagged medical texts using a tagged text generator 1, as discussed below.

Figure 1:
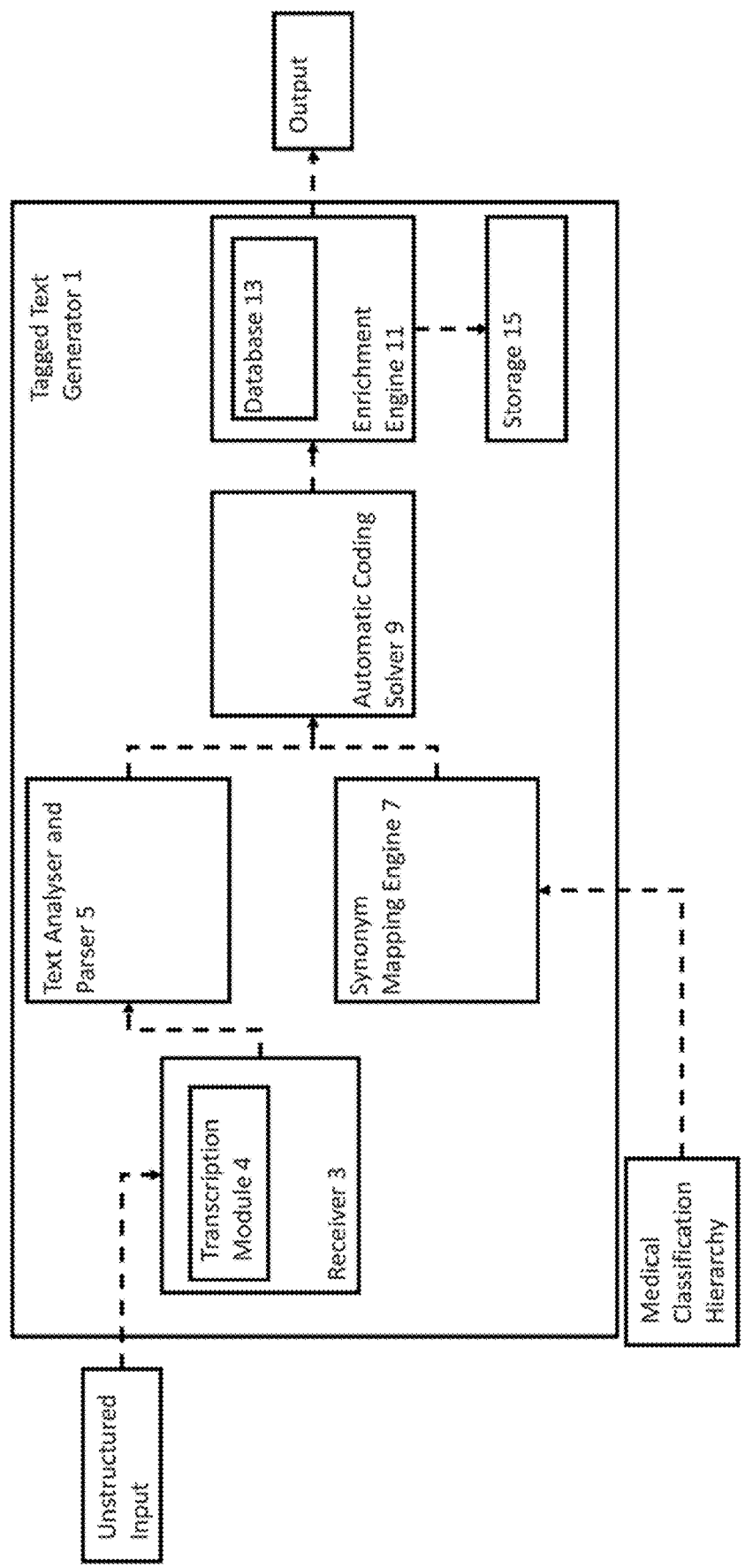
FIG. 1 is a schematic diagram of a tagged text generator in accordance with an aspect of an embodiment.

FIG. 1 shows an overview of the components in a tagged text generator 1 that is used to generate the tagged medical texts for subsequent curation and validation in an aspect of an embodiment. The tagged text generator 1 of FIG. 1 comprises: a receiver 3 (including a transcription module 4), an analyser and parser 5, a mapping engine 7, an automatic coding solver 9, an enrichment engine 11 (including a database 13) and storage 15. The components are discussed in detail below. Further, FIGS. 2A and 2B show a flowchart detailing a method of tagged medical text generation in accordance with an aspect of an embodiment.

Figure 2A:
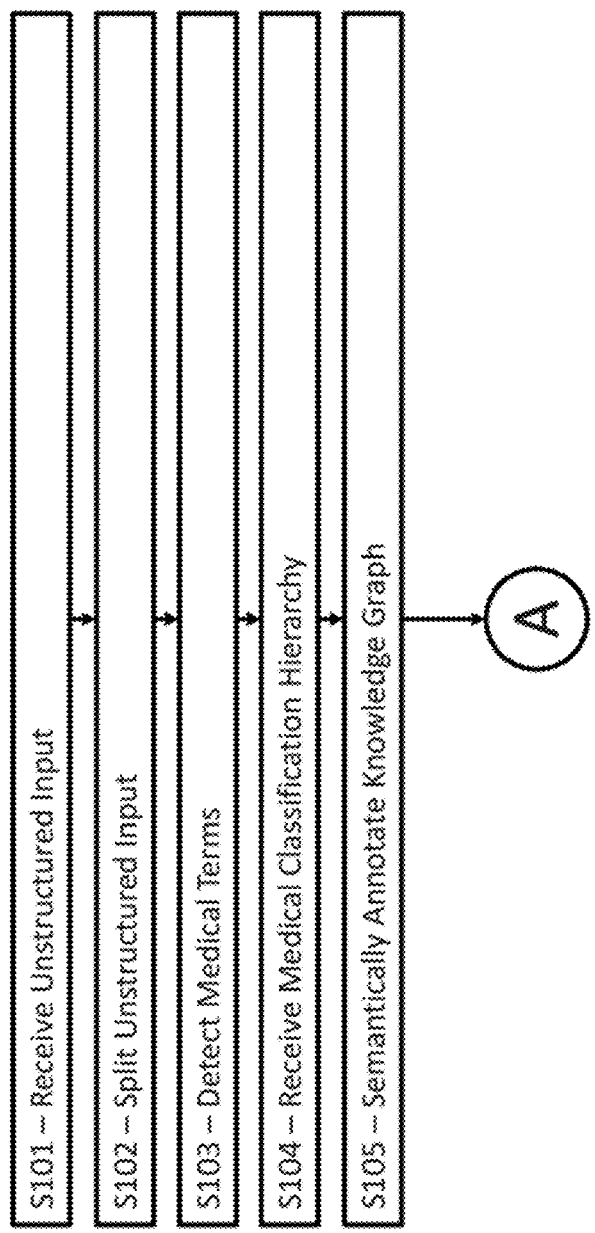
FIGS. 2A and 2B are a flowchart of a method of tagged text generation in accordance with an aspect of an embodiment.
Figure 2B:
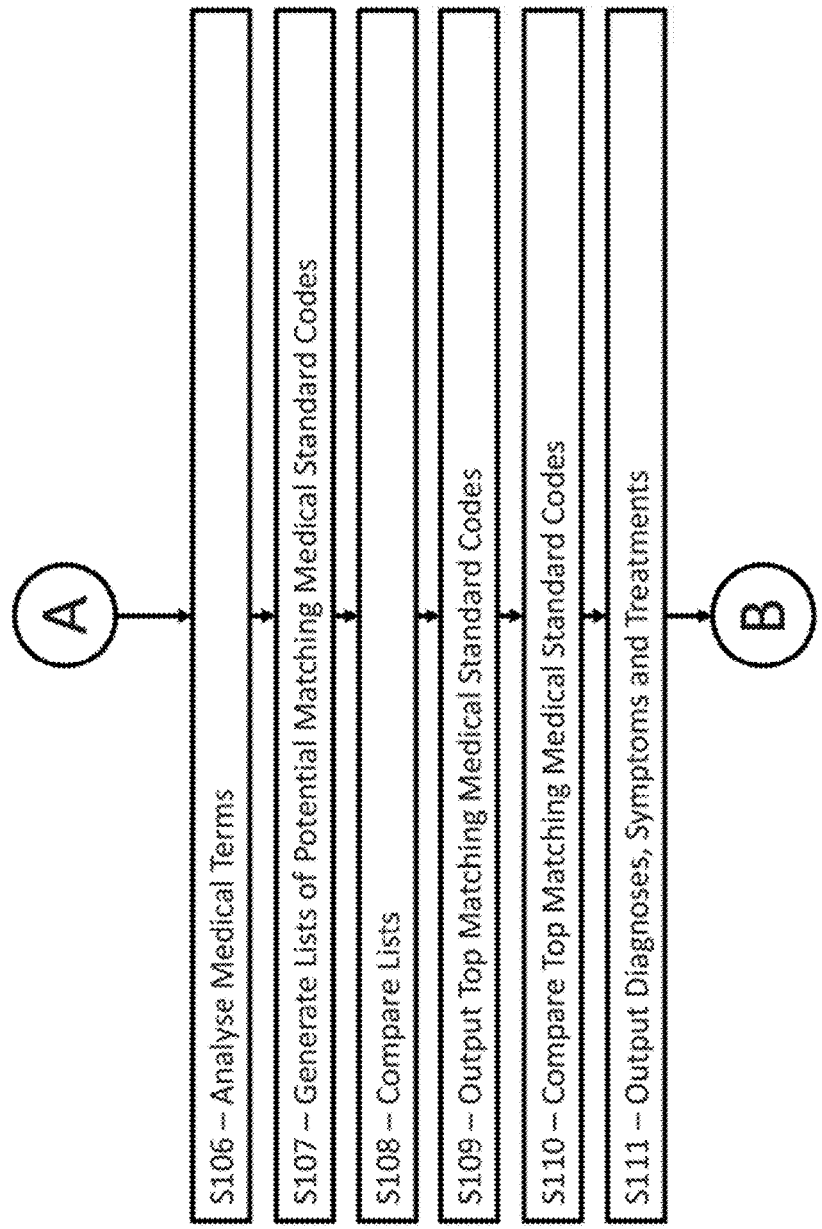

The tagged text generator 1 comprises a receiver 3 that is configured to receive an unstructured input, as shown in step S101 of FIG. 2A. The unstructured input comprises medical information relating to at least one patient. Although information relating to a plurality of patients may be combined into a single unstructured input, typically separate inputs are used for each patient for simplicity when associating standard medical codes with patients as discussed below. The inputs are referred to as "unstructured" because no specific template or format is used.

The receiver 3 may be configured to receive the unstructured input in a variety of different forms, depending on the type of unstructured input provided. Although the system may be configured to receive inputs from, for example, diagnostic tests, ECGs, etc., typically the unstructured inputs are records of patient consultations or clinical notes. The unstructured inputs generated from patient consultations or clinical notes are usually provided as either written information or as an audio recording. Audio recordings may comprise direct recordings of conversations between a medical practitioner and a patient, comments dictated by a medical practitioner (often following a consultation), or a combination of the two. Similarly, clinical notes may be either recorded during examinations (that is, clinical rounds), subsequently to the rounds, or a combination of the two. Where unstructured inputs are provided in written form, the inputs may be hand written or typed.

When unstructured inputs are input into the receiver 3, the receiver 3 may be configured to convert the unstructured inputs into a suitable format if necessary. For example, in aspects of embodiments configured to operate with unstructured inputs that are provided as audio files, the receiver 3 may comprise a transcription module 4 that is configured to convert audio files into text files. Further, in aspects of embodiments wherein handwritten unstructured inputs are provided (for example, as scans of handwritten pages), the receiver 3 may be further configured to perform text recognition to generate a text file.

The unstructured input received by the receiver 3 is then passed on to an analyser and parser 5, typically configured to operate using text unstructured inputs. The text analyser and parser 5 is configured to receive an unstructured input text file from the receiver 3 (the text file may have been generated from a further file type as discussed above). The text analyser and parser 5 is then configured to split the unstructured input into a plurality of logical components, as shown in step S102 of FIG. 2A. Typically the logical components are sentences, although other logical components may also be used. For example, where the text input file contains very long or very short sentences, or no punctuation, it may be appropriate to divide the text file into term groupings in another way.

Once the text input has been divided into logical components, the text analyser and parser 5 is configured to detect and extract from each logical component of the text any medical terms and entities that may be present (see step S103 of FIG. 2A). For this task, the text analyser and parser 5 is configured to use technologies such as OpenNLP frameworks, as are familiar to those working in the technical field. Part-of-Speech (POS) solutions may also be used to identify the type of the words; of particular relevance are substantives and nouns, the identification of which is necessary in order to extract the medical terms. Also, Named Entity Recognition (NER) systems may be used to detect several entities (e.g. diseases, chemicals, species or genes). Where a Named Entity Recognition system is used, this system may be a neural network trained with medical texts annotations to be able of extracting in new texts medical entities, building a Medical Named Entity Recognition (MNER) tool.

The output from the text analyser and parser 5 is the logical components, plus a set of candidate medical terms, nouns and medical entities detected in the logical components. These outputs are then passed to the automatic coding solver 9.

The automatic coding solver 9 receives the output from the text analyser and parser 5. A further input is received by the automatic coding solver 9 from a mapping engine 7, such as the synonym mapping engine 7 as discussed below.

The synonym mapping engine 7 is configured to receive at least one medical classification hierarchy, as shown in step S104 of FIG. 2A, from an external source such as a hierarchy database. The medical classification hierarchy details the links between the medical standard codes in a given medical classification scheme. As discussed above, the system may be configured to use any suitable medical classification, such as the ICD scheme, and may use a plurality of medical classifications. Once retrieved, one or more medical classification hierarchy may be retained by the synonym mapping engine 7.

Typically, the classification hierarchy is provided in the form of a knowledge graph; this is the most efficient way to detail the ontology of a medical classification hierarchy. A knowledge graph may represent the relationships between the different medical standard codes (relating to medical entities) forming a medical classification hierarchy, and may also be used to group the codes into categories, sub categories, and so on. For example, a category of "respiratory diseases" may have sub-categories of "asthma", "bronchitis", and so on. In turn, the sub-category of "asthma" may have further subsidiary categories of "exercise induced asthma", "nonallergic asthma", and so on. The terms "category", "sub category", etc. are used in a non-limiting sense, and do not imply the presence or absence of higher or subsidiary groupings.

Each of the medical entities may be treated as a node within the knowledge graph, with the relationships between entities indicated by vertices between nodes. Knowledge graphs may be used to represent ontologies using multi-dimensional plots, that is, graphically. While the synonym mapping engine 7 may receive the knowledge graph in a graphical format, the knowledge graph may also be received in another form, for example, as tabulated information.

When the synonym mapping engine 7 has received a medical classification hierarchy, this component is then configured to semantically annotate the knowledge graph, as shown in step S105 of FIG. 2A. The semantic annotation comprises enhancing the medical classification hierarchy with relevant additional information, such as synonyms of terms used in the description of the medical condition to which a given code relates, alternative names for the condition (if applicable), translations of the description into other languages, and so on. The new information is linked to each medical entity in order to extend the semantic data of the knowledge graph, thereby generating an extended knowledge graph for the given medical coding hierarchy. The synonyms may be provided with reference to any suitable database, such as the Ontology of Consumer Health Vocabulary, which is a SKOS-encoded implementation of the "Open Access, Collaborative Consumer Health Vocabulary Initiative" by the University of Utah. Enhancing the knowledge graph with synonyms increases the likelihood of correct matching between medical terms detected by the text analyser and parser 5 and the medical codes in the hierarchy. The enhanced knowledge graph is passed from the synonym mapping engine 7 to the automatic coding solver 9.

An example of a (truncated) entry in an extended knowledge graph for the condition "generalized anxiety disorder" is shown below:

Node (label: ICD9, ICD10, etc.)
code (e.g. F41.1)
description_en (e.g. Generalized anxiety disorder)
description_es (e.g. Trastorno de ansiedad generalizada)
description_ja (e.g. 全般性不安障害) synonyms_en (e.g. anxiety disorder generalize, anxiety disorder generalized, anxiety disorders generalized, gad, gads, generalised anxiety disorder, generalized anxiety disorders).

The automatic coding solver 9 receives the medical terms in the plurality of logical components from the text analyser and parser 5 and the enhanced knowledge graph from the synonym mapping engine 7. The medical terms are then compared against the enhanced knowledge graph, and a list of potential matching medical standard codes is generated for each of the medical terms. The lists of potential matching medical standard codes are then compared, and top matching medical standard codes are output based on the comparison.

Typically, the automatic coding solver 9 uses a probabilistic weighted-valued algorithm to return an ordered list of potential entity pairs of medical entity description with its standard codes (medical entity-codes); and a list of potential codes matching an input text in unstructured format (clinical note-codes). In order to improve the quality of the results generated, and increase the speed of subsequent calculations, the automatic coding solver 9 may pre-process the medical terms. This pre-processing may comprise converting the medical terms to their root terms, for example, using singular forms, lemmatization, stemming, and so on. The pre-processing may also or alternatively comprise identifying black-list terms, which may be terms that are too common in medical terminology to provide information useful for identifying potential matching medical standard codes, and removing these black-list terms before analysis.

Once pre-processing of the medical terms has been performed (if the automatic coding solver 9 is configured to use pre-processing), the medical terms are compared against the enhanced knowledge graph for the medical standard codes of the medical hierarchy, such that potentially matching medical standard codes may be identified (see steps S106 and S107 of FIG. 2B). The comparison may utilise string matching algorithms to identify the potentially matching medical standard codes such as, for example, Jaro-Winkler distance equations for the comparison of strings. The Jaro-Winkler distance equation for comparison of the similarity of two strings $s_1$ and $s_2$ is based on the Jaro similarity of the strings, ($sim_j$), which is given by the equation:

$$sim_j = \frac{1}{3}\left(\frac{m}{|s_1|} + \frac{m}{|s_2|} + \frac{m-t}{m}\right)$$

where m is the number of matching characters, that is, characters in $s_1$ and $s_2$ that are the same, and in the same location within the strings (a positive integer; if the number of matching characters is 0, then the value of $sim_j$ is also 0). The value of $|s|$ is the length of string s (that is, the number of characters in the string). Two characters are considered to be matching but transposed (that is, instances where the same character appears in the two strings but in different locations) if the equation $$\left\lfloor \frac{\max(|s_1|, |s_2|)}{2} \right\rfloor - 1$$

is satisfied, where max ($|s_1|$, $|s_2|$) returns a value of the length of the longer of the two strings. The value of t is half the number of transpositions.

The Jaro similarity is modified to obtain the Jaro-Winkler similarity ($sim_w$) The Jaro-Winkler similarity is given by the equation:

$$sim_w = sim_j + (lp(1-sim_j))$$

where l is the number of matching characters at the start of the two strings, to a maximum of 4 characters, and p is a scaling factor. The value of p is typically set at 0.1, and not higher than 0.25. The Jaro-Winkler similarity modifies the Jaro similarity to give greater weight to similarities at the start of pairs of strings, and is therefore helpful for identifying strings for related medical terms (for example, "bronchitis" and "bronchi"). Other string similarity measuring equations may be used, for example, Levenshtein distance measurements or Hamming distance measurements.

In some aspects of embodiments, the results from the comparisons between the medical terms and the medical standard codes may be further tested using a predetermined threshold. That is, the similarity values calculated using (for example) the Jaro-Winkler similarity measure may be compared to a matching threshold value, with only medical standard codes that generate similarity values that match or exceed the threshold considered to be potentially matching medical standard codes. In this way, the chances of incorrect matches and corresponding potential incorrect diagnosis advice are reduced.

In situations where similarity comparisons between a given medical term and the medical standard codes in a medical classification scheme do not result in any similarity values that satisfy the predetermined threshold, the automatic coding solver 9 may be configured to output a null result. That is, the automatic coding solver 9 may not output any potentially matching medical standard codes for the given medical term, and the given medical term may then be disregarded in subsequent processing. This configuration of the automatic coding solver 9 reduces the chances of incorrect top matching medical standard codes being output by the automatic coding solver 9 to the enrichment engine 11, but also means that information from the unstructured input may be lost (due to the medical term being essentially discarded from subsequent analysis). As an alternative response to situations where similarity comparisons between a given medical term and the medical standard codes in a medical classification scheme do not result in any similarity values that satisfy the predetermined threshold, the automatic coding solver 9 may output as a potentially matching medical standard code the medical standard code that generated the highest similarity value, despite this similarity value being below the predetermined threshold. Configuring the automatic coding solver 9 in this way reduces the chances of information from the unstructured input being lost, but may also increase the chances of an incorrect top matching medical standard code being passed to the enrichment engine 11.

The automatic coding solver 9 may be further configured, when performing the comparison between the medical terms and the medical standard codes, to separate the potential matching medical standard codes into a number of phrase categories based on relevance. That is, once identified as a potential matching medical standard code, each of the potential matching medical standard codes may be categorised, and this category information may subsequently be used when generating the top matching medical standard codes for the medical terms. In this way, information which is likely to ultimately be of more use for generating diagnosis information is passed to the enrichment engine 11.

Any number of categories may be used depending on the specific requirements of a given system, however large numbers of categories may result in the process of determining the top matching medical standard codes becoming excessively complex. A useful number of categories for most hierarchies is three. In an aspect of an embodiment, three categories are used: first phrases which are used in the description of a medical standard code; second phrases which are synonyms for phrases used in the description of a medical standard code; and third phrases which are general healthcare related phrases but are neither first phrases nor second phrases. In an example application of a three category system, if the description of a medical standard code for a given condition includes the phrase "abdominal pain", then potential matching medical standard code "abdominal pain" would be a first category phrase as this phrase appears directly in the description for the given condition. The potential matching medical standard code "stomach ache" is a synonym of the phrase that appears in the description, and therefore would be a second category phrase. The potential matching medical standard code "sickness" is a general phrase used in healthcare, but does not satisfy the criteria to be either a first or second category phrase for the given condition, and would therefore be a third category phrase.

It is possible that a potential matching medical standard code may relate to several different conditions and may be a different category phrase in relation to the different conditions. In this situation, the potential matching medical standard code may be considered separately with reference to each condition when the potential matching medical standard codes are evaluated to determine top matching medical standard codes.

Once the potential matching medical standard codes have been identified using similarity comparison and, if applicable, categorised into different phrase categories, the potential matching medical standard codes for each medical term detected in the unstructured input are then compared (see step S108 of FIG. 2B). The comparison is used to produce a list of top marching medical standard codes, which is then output, as shown in step S109 of FIG. 2B. A single consolidated list of top matching codes may be generated for the unstructured input as a whole, which increases the amount of medical terms that the top matching codes are based on (because codes from the entire unstructured input are used), and therefore increases the likelihood of the top matching codes accurately reflecting the content of the unstructured input.

A separate list of top matching codes may alternatively be generated for each logical component in the unstructured input, and the lists of top matching components may then be processed separately. Generating separate lists for the logical components increases the chance, in the event that the unstructured input relates to more than one medical condition, the different medical conditions are all detected. For example, if the unstructured input is written notes of a consultation between a medical practitioner and a patient which involved a discussion of two separate illnesses the patient is suffering from, generating separate lists of top matching components for each of the logical components (sentences in this case) of the unstructured input increases the chances of both illnesses being detected, because it is likely that at least some of the logical components will relate exclusively to only one of the illnesses. However, as the total number of detected medical terms used to generate each individual list of top matching codes is very likely to be lower than if a single consolidated list of top matching codes is generated from the unstructured input, the top matching generated codes are each based on less information and may not fully reflect the overall content of the unstructured input.

The top matching codes are generated by consolidating the potential matching standard codes (either for an entire unstructured input or per logical component, as discussed above). The consolidation generally comprises outputting the most commonly occurring potential matching standard codes, however the weighting of the potential matching medical standard codes (as discussed above) may also be taken into consideration. Where a number of the potential matching medical standard codes relate to the same medical condition (for example, all appear in the description of that condition), these codes may also be given extra weight when determining the top matching codes. Following the determination of the top matching codes, these codes are then output to the enrichment engine 11 for further processing (see step S109 in FIG. 2B).

An example of the process from the receiving of an unstructured input to the outputting of the top matching codes to the enrichment engine 11 is discussed below. In this example, the unstructured input is in the form of a clinical note that has been typed by a medical practitioner, in relation to the visit of a patient to a hospital. The raw unstructured input is shown below:

This 5-year-old male presents to Childrens Hospital Emergency Department by the mother with have asthma, Mother states he has been wheezing and coughing. They saw their primary medical doctor. He was evaluated at the clinic, given the breathing treatment and discharged home, was not having asthma prescribed prednisone and an antibiotic. They told to go to the ER if he got worse. He has had some vomiting and some abdominal pain. His peak flows on the morning are normal at 150, but in the morning, they were down to 100 and subsequently decreased to 75 over the course of the day. The differential entertained on this patient includes reactive airways disease viral syndrome, and foreign body pneumonia. He is evaluated in the emergency department with continuous high-dose albuterol, Decadron by mouth, pulse oximetry, and close observation. Chest x-ray reveals bronchial thickening, otherwise no definite infiltrate. She is further treated in the emergency department with continued breathing treatments. At 0048 hours, he has continued tight wheezes with saturations 99%, but ED sats are 92% with coughing spells. Based on the above, the hospitalist was consulted and accepts this patient for admission to the hospital with the working diagnosis of respiratory distress and asthma.

As the unstructured input is already in the form of a text file, it is not necessary for the receiver 3 to perform any conversion of the unstructured input. Instead, the receiver 3 transfers the unstructured input to the text analyser and parser 5. The text analyser and parser 5 then splits the unstructured inputs into logical components, in this example, sentences. The sentences are then analysed to detect and extract medical terms and entities. A list of the extracted medical terms and entities detected by the text analyser and parser 5 in the present example is shown below (for simplicity the list is shown in the order the medical terms and entities appear in the unstructured input):

asthma, wheezing, coughing, breathing treatment, asthma, prednisone, antibiotic, vomiting, abdominal pain, reactive airways disease, viral syndrome, foreign body pneumonia, continuous high-dose albuterol, Decadron by mouth, pulse oximetry, chest x-ray, bronchial thickening, continued breathing treatments, continued tight wheezes, coughing spells, respiratory distress, asthma.

The detected medical terms are then passed to the automatic coding solver 9. The automatic coding solver 9 has received a medical classification hierarchy from the synonym mapping engine 7, wherein the medical classification hierarchy has been enhanced as discussed above. In this example, the ICD-10 medical classification hierarchy is used.

Having received the extracted medical terms and entities from the text analyser and parser 5, the automatic coding solver 9 in the present example pre-processes the extracted medical terms and entities. For example, the terms "wheezing" and "wheezes" would both be pre-processed to return the root term "wheeze". The automatic coding solver 9 in the present example then performs similarity comparisons for the extracted medical terms using the Jaro-Winkler similarity equation. Potential matching medical standard codes are identified based on the similarity comparisons: example results for the medical terms "asthma", "abdominal pain" and "respiratory distress" are shown below, along with the calculated $sim_w$ values:

asthma
    J45 (Asthma): value 1.0
    J46(Status asthmaticus): value 1.0
    J45.0(Predominantly allergic asthma): value 0.6 abdominal pain
    R10.4(Other and unspecified abdominal pain): value 0.6
    R10(Abdominal and pelvic pain): value 0.4 respiratory distress
    J80(Adult respiratory distress syndrome): value 0.6
    P22(Respiratory distress of newborn): value 0.6
    P22.0(Respiratory distress syndrome of newborn): value 0.6

For brevity, the potential matching medical standard codes for all of the medical terms are not shown. In the examples shown above, both categories (such as J45 and R10) and corresponding sub categories (such as J45.0 and R10.4 respectively) are present; the automatic coding solver 9 may link or consolidate these terms when determining and outputting the top matching medical standard codes. Also, the results shown above have already been subjected to the predetermined threshold as discussed above; results which did not satisfy the threshold are not presented.

In the present example, the automatic coding solver 9 is configured to output top matching medical standard codes for the unstructured input as a whole. Based on an analysis of all of the potential matching medical standard codes, the automatic coding solver 9 outputs the following top matching medical standard codes for the unstructured input:

J45(Asthma)
    J80(Adult respiratory distress syndrome)
    R10.4(Other and unspecified abdominal pain)

The above example considers a situation in which three top matching medical standard codes are output by the automatic coding solver 9; larger or smaller numbers of codes may be output depending on the specific system configuration.

The output from the automatic coding solver 9 is passed to the enrichment engine 11 (as discussed above, see step S109 in FIG. 2B). The enrichment engine 11 comprises or is linked to a database 13 linking diagnoses, symptoms and treatments. Typically, the diagnoses in the database 13 are linked to corresponding medical standard codes using the same medical hierarchy as used by the synonym mapping engine and automatic coding solver 9. In examples wherein the database 13 used by the enrichment engine 11 comprises medical standard codes from a different medical hierarchy to those used by the synonym mapping engine and automatic coding solver 9, or the database 13 does not comprise medical standard codes, it is necessary to retrieve information from the database 13 using medical condition names or a conversion table converting between different medical hierarchies; both of these options are less efficient than using the same medical hierarchy in the database 13, the synonym mapping engine 7 and the automatic coding solver 9.

The database 13 may be compiled from collected and anonymised patient health records, medical textbooks and journal papers, entries by medical personnel, and so on. Each entry for a given medical condition (such as a disease) may be enhanced with information on related conditions, such as: conditions which may be mistaken in medical examination for the given medical condition; conditions which may trigger development of the given medical condition; conditions which may result from the given medical condition, and so on. The entries may also be linked to information on symptoms which may be used to help diagnose given medical conditions, and treatments which a medical practitioner may apply in order to relieve the symptoms of a given medical condition and/or cure the medical condition. Further information may also be provided if available, for example, if various treatments are available and are suitable for different types of patients (such as patients having certain allergies, infants, expectant mothers, and so on), this information may also be provided. The enrichment engine 11 may be configured to compile the database 13 from individually entered pieces of information (such as anonymised patient health records), or a completed database 13 may be uploaded to the enrichment engine 11.

Figure 3:
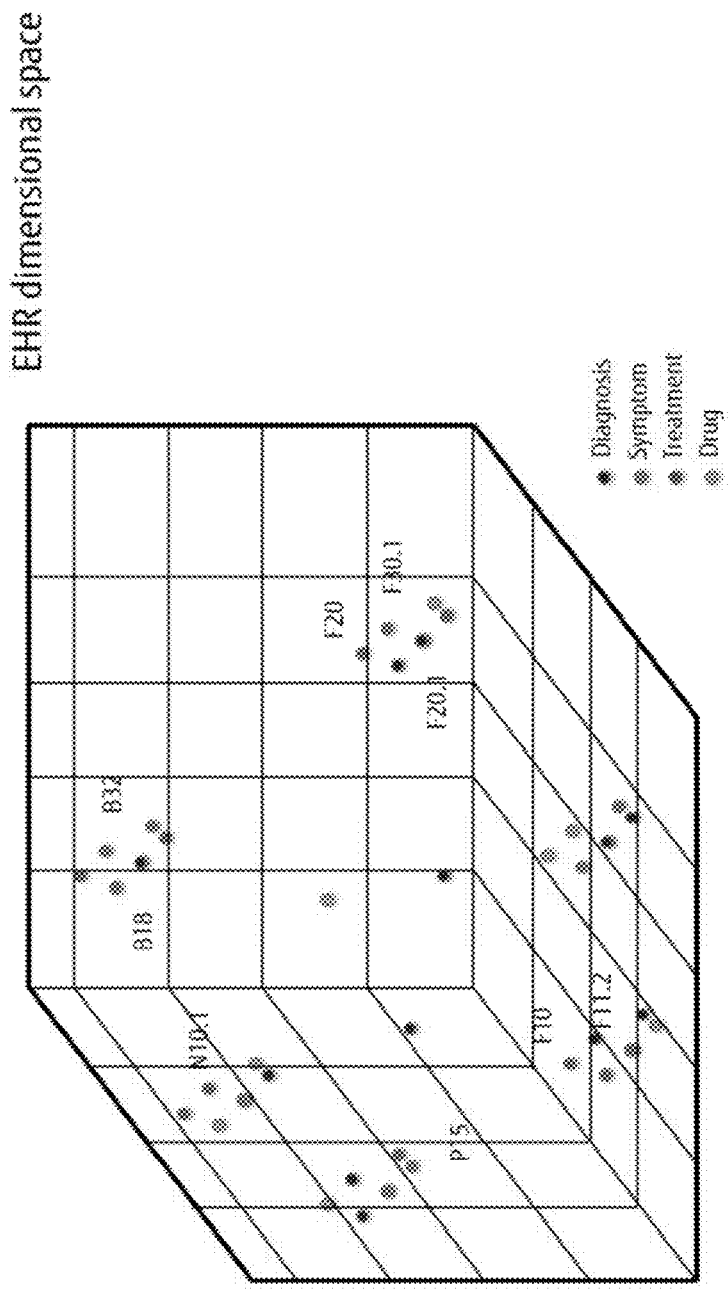
FIG. 3 is a diagram of a biomedical entity matrix.

The database 13 may be stored in any suitable format. One option is to use a series of anonymised patient health records to form a word embedding matrix, containing diagnoses, treatments, symptoms, procedures, drugs, etc. from the anonymised patient health records, and then using the word embedding matrix to create a biomedical entity matrix that links together the diagnoses, treatments, symptoms, procedures, drugs, etc. in a format that may be searched using the top matching medical standard codes. An example of a biomedical entity matrix is shown in FIG. 3. A biomedical entity matrix may be created using, for example, a skip-gram model. The skip-gram is model architecture for word embedding (i.e. to define distributed and correlated representation of words). The main characteristic of skip-gram model when iterating over the words of each sentence is that it uses the current word to predict its neighbours and in this way try to know the context.

When the enrichment engine 11 receives the top matching medical standard codes relating to a given unstructured input, the enrichment engine 11 queries the database 13 using the top matching medical standard codes and retrieves diagnoses, symptom and treatment information relating to the top matching medical standard codes (see step S110 in FIG. 2B). The enrichment engine 11 may also be linked to other information sources, such as a patient records repository. In some aspects of embodiments, the enrichment engine 11 may access the specific medical record linked to a patient that is the subject of the unstructured input, and extract medical standard codes from the specific medical record, and to take the extracted medical standard codes into account when retrieving diagnoses, symptoms and treatments. The enrichment engine 11 may be further or alternatively configured to update the specific medical record with determined diagnoses, symptoms and treatments.

Once the diagnoses, symptoms and treatments have been retrieved, the enrichment engine 11 enriches the unstructured text by tagging the text (that is, modifying or creating metadata tags for the text) indicating the top matching medical standard codes, and may also tag the text with the diagnoses, symptoms and treatments. In this way, the medical texts tagged with potential medical codes may be generated for sending to a further receiver 23 (see FIG. 4).

The diagnostic aid may be further configured to store the unstructured input in suitable storage 15, in conjunction with the top matching tags and (optionally) diagnoses, symptoms and treatments. The storage 15 may form part of the tagged text generator 1, or may be a separate storage unit connected to the tagged text generator 1 by a suitable data connection, such as the Internet. In this way, a plurality of input medical texts tagged with potential medical codes may be generated for bulk submission to the further receiver 23.

FIG. 4 shows a diagram of a medical diagnostic aid 21 in accordance with an aspect of an embodiment. The operation of the medical diagnostic aid 21 is discussed with reference to the flowchart in FIGS. 5A and 5B. The medical diagnostic aid 21 comprises a tagged text generator 1, such as the tagged text generator 1 discussed above, which is configured to output tagged medical texts to the receiver 23 wherein the medical texts are tagged (at least) with potential medical codes. As discussed above, the tagged medical texts may be created by human tagging of medical texts, or using the tagged text generator 1 shown in FIG. 1. The tagged medical texts may be received individually, or a plurality of tagged texts may be received simultaneously (see step S501 in FIG. 5A). The receiver 23 may be further configured to store the tagged medical texts (for example, in a connected storage unit) until a preset number of tagged medical texts are received, which can then be transferred for further processing. Typically, the tagged medical texts are received electronically using a suitable network, such as the Internet or a LAN, or from a tagged text generator 1 that is a component of the diagnostic aid 21.

When the receiver 23 has received a plurality of tagged medical texts, the texts are then sent to the data curator 25. The data curator 25 is configured to curate and validate the plurality of input tagged medical texts (see steps S502 and S503 in FIG. 5A), to thereby generate a subset of medical texts that are validated and tagged with medical codes that have been confirmed. If diagnoses, symptoms and treatment information is also included in the tags, this may also be confirmed during the curation and validation process. The curation and validation of the medical texts uses human input. Although the curation and validation may be done by a single individual (with sufficient medical knowledge), it is typically faster and more efficient if the curation and validation is performed by a group of suitably knowledgeable persons. As such, in an aspect of an embodiment, the data curator 25 comprises components for controlling crowdsourced curation and verification of the medical texts.

Crowdsourcing is an effective and efficient method for recruiting and paying subjects, known as workers. It is important to highlight that "paying" (or "incentive") do not refer exclusively to financial compensation, but rather refer to any incentive a worker may be given to engage with a task.

In an example, the data curator 25 receives a set of already tagged clinical notes, and allows the selection, curation, and validation of those notes by the "crowd". In this context, the "crowd" are a set of mid-level, and senior-level medical resident doctors, along with their senior doctors. This is because medical knowledge useful in order to perform the curation and validation tasks.

Although the curation and validation may comprise a single stage, that is, review by a single person of each medical text, ideally plural stages of curation and validation are used. In an aspect of an embodiment, the curation and validation comprises at least an initial stage (in which curation decisions are made) and a final stage (in which the decisions made in the initial stage are checked and validated). It is useful if the personnel involved in the final stage are senior, or experienced, medical personnel. To reduce the demands on the time of experienced personnel, comparatively inexperienced medical personnel may be used in the initial stage. Where comparatively inexperienced medical personnel are used in the initial stage, these inexperienced medical personnel may be selected for the role by more experienced personnel, such as the personnel involved in the final stage.

The curation of the tagged medical texts may involve automatic processes, that is, processes which may be performed without human input. For example, where a large number of tagged medical texts are received by the receiver 23, the data curator 25 may filter the tagged medical texts based on factors such as: the number of potential medical codes associated with the text, the language the text is written in, the length of the text, and so on. That is, the data curator 25 may remove (without requiring human input) texts that contain incomplete information, either because the texts do not have any tags or medical terms, or include one or more medical terms, but do not include any tags, or include one or more tags, but do not have any related medical terms. The data curator 25 may also or alternatively remove texts that are not written in a working language of the medical personnel to be involved in curation and validation, for example, may remove a Spanish text if the working language is English. The data curator 25 may also or alternatively remove texts which are below a length threshold, for example, which have only one sentence in total.

In an example, the remaining tagged medical texts may then be curated, by means of reviewing the biomedical entities linked with the text of the clinical notes. The curation task may be posted on a Hospital Information System, with the corresponding description of the task and all the necessary information, if available. In the present example, the workers for the curation are mid-level medical resident doctors. A senior doctor may oversee the distribution of the tagged medical texts to the mid-level medical doctors.

In the curation, the mid-level medical resident doctor may assess the tagged medical texts to: check the coverage of the medical terms for the medical text, and validate that the medical terms are correct; check the coverage of the attached tags; add or remove any incorrect medical terms or tags; report any changes made, and save an original and validated version of the tagged medical text. For the purposes of performance tracking, the medical personnel may also include their identification information as reviewer of the medical text.

Multiple stages of curation may be performed, by different personnel, to increases the chances of erroneous decisions being identified.

Following the curation, the curated tagged medical texts may then be validated. The validation stage may involve a more experienced/senior medical professional reviewing the curation decisions, and correcting any errors detected.

The output from the data curator 25 is a subset of the tagged medical texts, that has been curated and validated and is therefore highly likely to have correct tags. The subset of tagged medical texts may then be input into a classification model engine 27 that is configured to use the tagged medical texts to generate a medical text learning model.

Figure 5A:
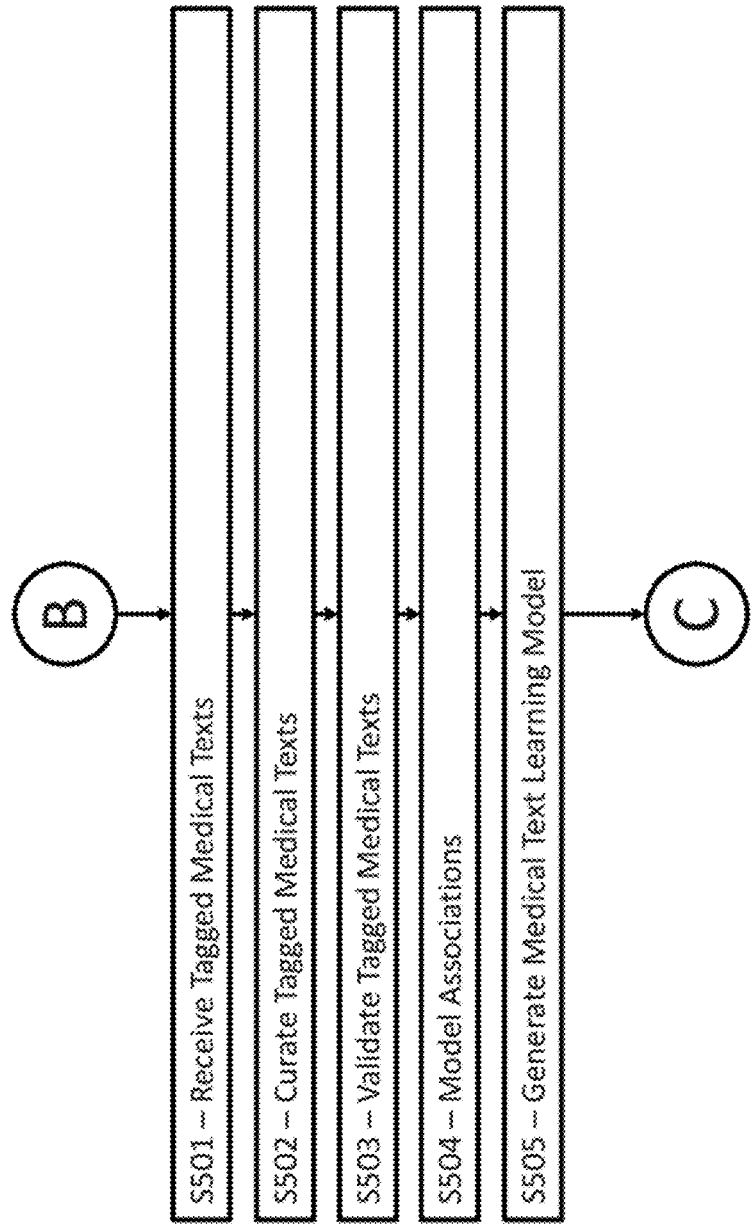

In an aspect of an embodiment, the classification model engine 27 may use machine learning and deep learning technologies to build the model that will allow the automatic analysis of medical texts (see step S504 in FIG. 5A). In this context, the component may rely on topic modelling algorithms, such as Labelled Latent Dirichlet Allocation (L-LDA) modelling, to learn associations between text of the medical texts and medical codes (in the tags) and materialize those associations as low level representations of words, i.e., word embeddings. The generated medical text learning model may rely upon deep learning techniques, in particular on applying Convolutional Neural Networks (CNN) to the word embeddings to create the model to assign tags (comprising medical codes) to future medical texts.

Latent Dirichlet Allocation (LDA) is a statistical method that analyses the words of texts to discover themes that run through them, how those themes are connected to each other, and how they change over time. In particular, LDA is a generative statistical model that allows sets of observations to be explained by unobserved groups that explain why some parts of the data are similar. For example, if observations are words collected into documents, LDA posits that each document is a mixture of a small number of topics and that each word's creation is attributable to one of the document's topics. In the present example the topics are the medical codes associated with the (curated and validated) medical texts. LDA can be used to identify topics that are present in any given document by observing all the words in it and producing a topic distribution. The only observable features LDA sees are the words appearing in a set of documents, and other parameters are hidden or latent: One of those hidden parameters is a topic that is assigned to each word thus making every document a mixture of those topics. Labelled LDA is a specific type of LDA, wherein some topic knowledge is provided to the model, in the present example, through the use of curated and validated medical codes associated with the medical texts.

The L-LDA model may output a biomedical entity distribution for given medical codes. For example, and with reference to the ICD-10 code J45.0 (for "asthma") as discussed above, relations between this code and various terms may be determined as shown below, wherein higher values indicate increased likelihood of the code applying to the text if the term is present:

asthma—0.832
allergic—0.822
respiratory illness—0.764
respiratory disorder—0.772

The biomedical entity distribution may be provided in the form of a space matrix representation (R) of the word embeddings. This information can then be used to train a convolutional neural network (CNN) to assign medical codes (see step S505 in FIG. 5A). In an example, the CNN has one input layer, one convolution layer, one sub-sampling layer and one fully connected layer. Although one output neuron with sigmoid or tanh function is sufficient for binary classification, multiple neurons with softmax function may be used to facilitate the use of CNN models for multi-class classification, multi-label classification, which is appropriate in the present implementation as several medical codes may ultimately be associated with a given medical text. The details of each layer are described briefly below.

The Input layer receives a sentence consisting of n words. Formally, $x_i \in R^k$ is a k-dimensional word representation for the ith word in the sentence, with reference to the space matrix representation R. A sentence of length n is then denoted as $X_{1:n} = x_1 \oplus x_2 \oplus \ldots \oplus x_n$, where $\oplus$ is a concatenation operator. As such, each input sentence is represented as n x k matrix. Typically, short sentences may be padded with zeros, so that all the matrices for a medical text share the same size.

The convolution layer applies a convolution filter $w \in R^{h \times k}$, which is applied to a window of h words of k-dimensional embeddings and produces a new feature. For instance, given a windows of words $X_{i:i+h-1}$ and a bias term $b \in R$, a new feature $c_i$ is generated by $c_i = f(w \cdot X_{i:i+h-1} + b)$, where f is a non-linear function. In the present example the element-wise function Rectified Linear Unit (ReLU) is applied to the input matrices, as would be understood by one skilled in the art of neural networks.

The sub-sampling layer applies a sub-sampling method, such as average pooling, median pooling, and max pooling. In the present example, max pooling is applied over each feature map produced by the convolution layer to obtain the maximum element c'=max {c}. The maximum element is then used as an input for the fully connected layer.

Given c' as the input, the fully connected layer produces $P(Y=c|c'\theta)=\text{softmax}_i(W \cdot (c' \text{ or }) b)$, where Y is the prediction, $\theta$ denotes parameters {W,b}, W denotes weights, o denotes the element-wise multiplication operator and $r \in R^m$ is a dropout mask vector of Bernoulli variables with probability p of being zero. The fully connected layer has the set of Biomedical Entities in which the input text will be classified. In this way, the medical text learning model may be generated based on the input (validated and curated) medical texts tagged with medical codes.

The medical text learning model, once generated, may then be used to analyse new medical texts and identify suggested medical codes based on the medical texts. An inputter 29 may be used to input a specimen text (see step S506 in FIG. 5B), such as (not annotated) notes from a patient consultation. As is the case with the receivers, typically the notes will be input electronically, either over a suitable network or entered directly into the inputter 29 by a medical practitioner using a keyboard or via a dictation (which may then be converted into a text file as discussed above).

When the notes have been input, a processor may be used to process the note text using the medical text learning model established as discussed above, as shown in step S507 in FIG. 5B. The model may be used to analyse the note text and suggest medical codes based on the note text. The processor may also enhance the note text with the suggested codes, that is, add the codes to the metadata of the note text.

The medical codes suggested by the processor may then be used by the outputter 33 to retrieve diagnoses, symptoms and treatments linked to the suggested medical codes, as shown in step S508 in FIG. 5 Boutputter 33. Typically, the diagnoses, symptoms and treatments are retrieved from a database 13, such as the database 13 used in an aspect of an embodiment by the enrichment engine.

The diagnoses, symptoms and treatments, once retrieved, may then be output directly to a medical professional (such as the professional responsible for inputting the specimen text), as shown in step S509 in FIG. 5B. The diagnoses, symptoms and treatments may also be retained for subsequent analysis.

The medical diagnostic aid 21 may automate the analysis of unstructured inputs, and may therefore save time and effort for the medical practitioner, and also provide the medical practitioner with information which may not otherwise have been discovered by the medical practitioner. Also, the curation and verification of the plurality of input medical texts tagged with potential medical codes prior to the generation of the medical text learning model increases the accuracy of the dataset used to generate the model, and thereby increases the accuracy of the diagnoses, symptoms and treatments provided using the suggested medical codes from the model.

Figure 6:
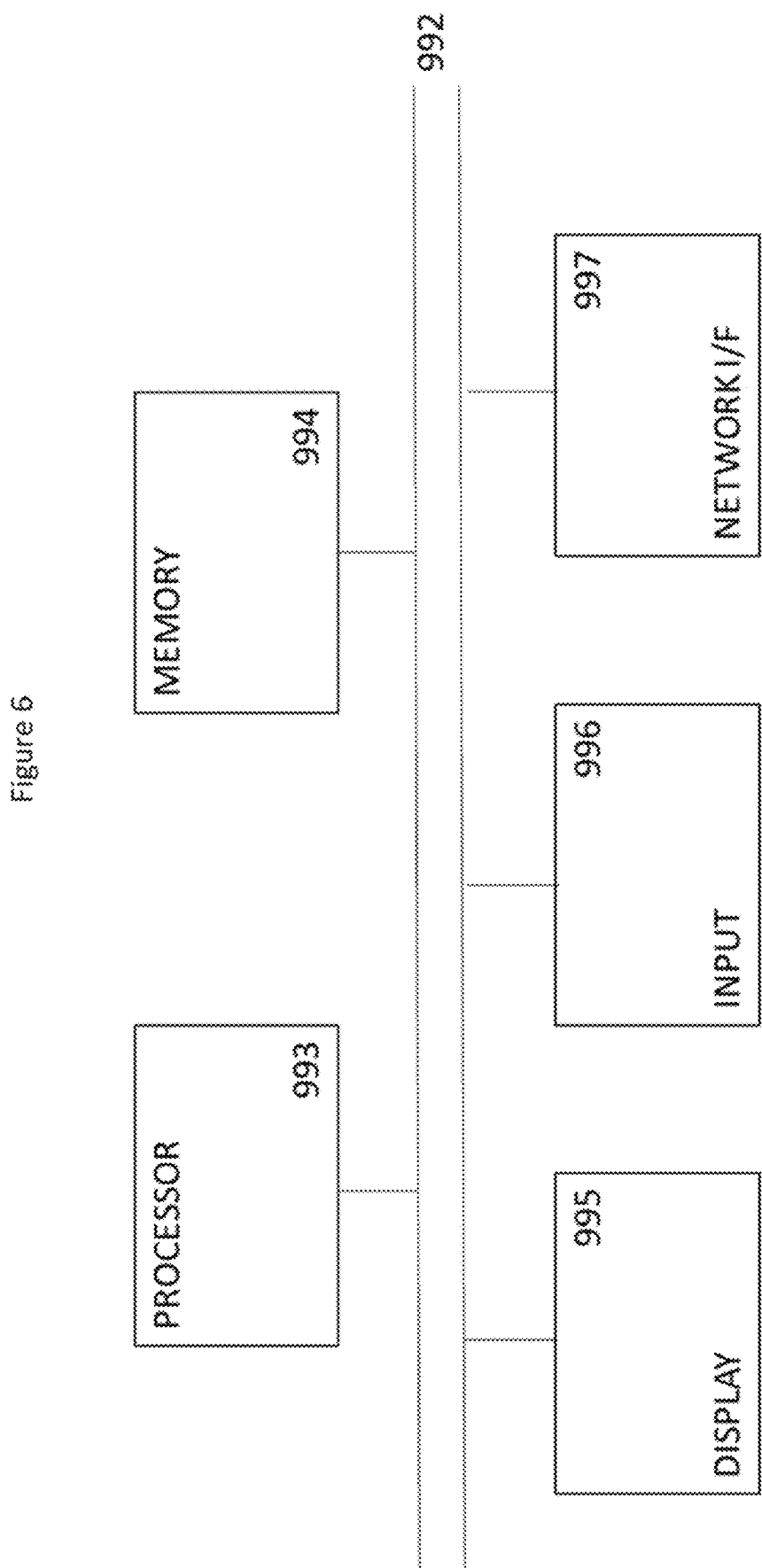
FIG. 6 block diagram of a computing device which embodies an embodiment.

FIG. 6 is a block diagram of a computing device, such as a personal computer, which embodies an example, and which may be used to implement an embodiment of the method for assisting medical personnel in performing a diagnosis. The computing device comprises a processor 993, and memory 994. Optionally, the computing device also includes a network interface 997 for communication with other computing devices, or for communicating with remote databases.

An example may be composed of a network of such computing devices, such that components of the diagnostic aid 21 are split across a plurality of computing devices. Optionally, the computing device also includes one or more input mechanisms such as keyboard and mouse or touchscreen interface 996, and a display unit such as one or more monitors 995. The components are connectable to one another via a bus 992.

The memory 994 may include a computer readable medium, which term may refer to a single medium or multiple media (e.g., a centralized or distributed database and/or associated caches and servers) configured to carry computer-executable instructions or have data structures stored thereon. The memory 994 may be the same memory 9 as may be used for storage, or a separate memory. Computer-executable instructions may include, for example, instructions and data accessible by and causing a general purpose computer, special purpose computer, or special purpose processing device (e.g., one or more processors) to perform one or more functions or operations. Thus, the term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media. By way of example, and not limitation, such computer-readable media may include non-transitory computer-readable storage media, including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices). In particular, the computer readable medium may comprise a computer program which, when executed on a computer, causes the computer to perform a method for assisting medical personnel in performing a diagnosis as discussed above.

The processor 993 is configured to control the computing device and execute processing operations, for example executing code stored in the memory to implement the various different functions of the receiver, text analyser and parser, synonym mapping engine, automatic coding solver and enrichment engine described here and in the claims. The memory 994 stores data being read and written by the processor 993. As referred to herein, a processor may include one or more general-purpose processing devices such as a microprocessor, central processing unit, or the like. The processor may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also include one or more special-purpose processing devices such as an application specific integrated circuit (ASIC), a field programmable gate array (FPGA), a digital signal processor (DSP), network processor, or the like. In one or more embodiments, a processor is configured to execute instructions for performing the operations and steps discussed herein.

The display unit 997 may display a representation of data stored by the computing device and may also display a cursor and dialog boxes and screens enabling interaction between a user and the programs and data stored on the computing device. The display unit may also comprise a touchscreen interface. The input mechanisms 996 may enable a user to input data and instructions to the computing device.

The network interface (network I/F) 997 may be connected to a network, such as the Internet, and is connectable to other such computing devices via the network. The network I/F 997 may control data input/output from/to other apparatus via the network. The network interface may also be used in receiving unstructured inputs medical classification hierarchies, tagged medical texts, specimen notes, and so on. The network interface may also be used for transmitting diagnoses, symptoms and treatments.

Other peripheral devices such as microphone, speakers, printer, power supply unit, fan, case, scanner, trackerball etc. may be included in the computing device.

The receiver 3 of FIG. 1 may be a processor 993 (or plurality thereof) executing processing instructions (a program) stored on a memory 994 and exchanging data via a network 997 or bus 992. In particular, the processor 993 may execute processing instructions to receive an unstructured input. Furthermore, the processor 993 may execute processing instructions to send the unstructured input to other components within the diagnostic aid 21, such as the text analyser and parser 5, or to store the unstructured input in the storage.

The text analyser and parser 5 of FIG. 1 may be a processor 993 (or plurality thereof) executing processing instructions (a program) stored on a memory 994 and exchanging data via a network 997 or bus 992. In particular, the processor 993 may execute processing instructions to split the unstructured input into a plurality of logical components, and to detect medical terms in the plurality of logical components as discussed above. Furthermore, the processor 993 may execute processing instructions to send an output to other components within the diagnostic aid 21, such as the automatic coding solver 9.

The synonym mapping engine 7 of FIG. 1 may be a processor 993 (or plurality thereof) executing processing instructions (a program) stored on a memory 994 and exchanging data via a network I/F 997 or bus 992. In particular, the processor 993 may execute processing instructions to receive a medical classification hierarchy of medical standard codes in the form of a knowledge graph, and semantically annotate the knowledge graph with synonyms of medical terms used in the medical standard codes as discussed above. Furthermore, the processor 993 may execute processing instructions to send the knowledge graph to other components within the diagnostic aid 21, such as the automatic coding solver 9.

The automatic coding solver 9 of FIG. 1 may be a processor 993 (or plurality thereof) executing processing instructions (a program) stored on a memory 994 and exchanging data via a network I/F 997 or bus 992. In particular, the processor 993 may execute processing instructions analyse the medical terms detected in the plurality of logical components, to generate a list of potential matching medical standard codes for each of the medical terms, to compare the lists of potential matching medical standard codes, and to output top matching medical standard codes based on the comparison as discussed above. Furthermore, the processor 993 may execute processing instructions to send the top matching medical standard codes to other components within the diagnostic aid 21, such as the enrichment engine 11.

The enrichment engine 11 of FIG. 1 may be a processor 993 (or plurality thereof) executing processing instructions (a program) stored on a memory 994 and exchanging data via a network I/F 997 or bus 992. In particular, the processor 993 may execute processing instructions to compare the top matching medical standard codes output by the automatic coding solver against entries in the database of diagnoses. Furthermore, the processor 993 may execute processing instructions to output medical text enriched with top matching medical standards codes to a receiver 23.

The receiver 23 of FIG. 4 may be a processor 993 (or plurality thereof) executing processing instructions (a program) stored on a memory 994 and exchanging data via a network I/F 997 or bus 992. In particular, the processor 993 may execute processing instructions to receive a plurality of input medical texts tagged with potential medical codes. Furthermore, the processor 993 may execute processing instructions to output the plurality of input medical texts tagged with potential medical codes to a data curator 25.

The data curator 25 of FIG. 4 may be a processor 993 (or plurality thereof) executing processing instructions (a program) stored on a memory 994 and exchanging data via a network I/F 997 or bus 992. In particular, the processor 993 may execute processing instructions to curate and validate the plurality of input medical texts. Furthermore, the processor 993 may execute processing instructions to output a subset of medical texts that are validated and tagged with medical codes to a classification model engine 27.

The classification model engine 27 of FIG. 4 may be a processor 993 (or plurality thereof) executing processing instructions (a program) stored on a memory 994 and exchanging data via a network I/F 997 or bus 992. In particular, the processor 993 may execute processing instructions to use the subset of tagged and validated medical texts to model the associations between the medical texts and the medical codes, and to generate a medical text learning model based on the associations. Furthermore, the processor 993 may execute processing instructions to output the medical text learning model to a specimen text processor 31.

The inputter 29 of FIG. 4 may be a processor 993 (or plurality thereof) executing processing instructions (a program) stored on a memory 994 and exchanging data via a network I/F 997 or bus 992. In particular, the processor 993 may execute processing instructions input a specimen text relating to a patient into the medical text learning model.

The specimen text processor 31 of FIG. 4 may be a processor 993 (or plurality thereof) executing processing instructions (a program) stored on a memory 994 and exchanging data via a network I/F 997 or bus 992. In particular, the processor 993 may execute processing instructions to process the specimen text using the medical text learning model, and identify suggested medical codes based on the specimen text. Furthermore, the processor 993 may execute processing instructions to output the suggested medical codes to the outputter 33.

The outputter 33 of FIG. 4 may be a processor 993 (or plurality thereof) executing processing instructions (a program) stored on a memory 994 and exchanging data via a network I/F 997 or bus 992. In particular, the processor 993 may execute processing instructions to retrieve from a database 13 diagnoses, symptoms and treatments linked to the suggested medical codes. Furthermore, the processor 993 may execute processing instructions to output diagnoses, symptoms and treatments linked to the suggested medical codes for assisting medical personnel in providing a diagnosis for the patient.

Exemplary methods may be carried out on one or more computing devices such as that illustrated in FIG. 6. Such a computing device need not have every component illustrated in FIG. 6, and may be composed of a subset of those components. A method may be carried out by a single computing device in communication with one or more data storage servers via a network, as discussed above. The scope of the invention is defined by the claims.

The invention claimed is:

1. A method for assisting medical personnel in performing a diagnosis, the method comprising an initialisation step and a diagnostic step,
   wherein the initialisation step comprises:
   receiving a plurality of input medical texts tagged with potential medical codes;
   curating and validating the plurality of input medical texts to output a subset of medical texts that are validated and tagged with medical codes; and
   using the subset of tagged and validated medical texts to model the associations between the medical texts and the medical codes, and generating a medical text learning model based on the associations, wherein the associations between the medical texts and the medical codes for the tagged and validated medical texts are modelled using a Labelled Latent Dirichlet Allocation topic model, and wherein the medical text learning model uses a convolutional neural network, and
   wherein the diagnostic step comprises:
   inputting a specimen text relating to a patient into the medical text learning model;
   processing the specimen text using the medical text learning model;
   identifying suggested medical codes based on the specimen text; and
   outputting diagnoses, symptoms and treatments linked to the suggested medical codes for assisting medical personnel in providing a diagnosis for the patient.

2. The method of claim 1, wherein the curation and validation of the plurality of input medical texts comprises selecting the subset of medical texts based on at least one of:
   the number of potential medical codes associated with text;
   the language text is written in; and
   the length of text.

3. The method of claim 1, wherein the curation and validation involves input from medical personnel.

4. The method of claim 3, wherein the curation and validation comprises at least an initial stage and a final stage, wherein medical personnel involved in the initial stage are less experienced than medical personnel involved in the final stage, and wherein the medical personnel involved in the final stage select medical personnel for involvement in the initial stage.

5. The method of claim 1, wherein the plurality of input medical texts are natural language texts.

6. The method of claim 5, wherein the natural language texts are notes relating to a patient consultation.

7. The method of claim 1, further comprising generating the plurality of input texts tagged with potential medical codes by:
receiving an unstructured input;
splitting the unstructured input into a plurality of logical components, and detecting medical terms in the plurality of logical components;
receiving a medical classification hierarchy of medical standard codes in the form of a knowledge graph, and semantically annotating the knowledge graph with synonyms of medical terms used in the medical standard codes;
analysing the medical terms detected in the plurality of logical components by a text analyser and parser, generating a list of potential matching medical standard codes for each of the medical terms, comparing the lists of potential matching medical standard codes, and outputting top matching medical standard codes based on the comparison; and
inputting the unstructured input tagged with the top matching medical standard codes as one of the plurality of input medical texts.

8. The method of claim 7, wherein the step of inputting of the specimen text comprises accessing a medical record linked to a patient that is the subject of the specimen text, and the outputting diagnoses, symptoms and treatments linked to the suggested medical codes for assisting medical personnel in providing a diagnosis for the patient further comprises outputting the medical record.

9. The method of claim 8, further comprising updating the medical record with the output diagnoses, symptoms and treatments.

10. A medical diagnostic aid for assisting medical personnel in performing a diagnosis, the diagnostic aid comprising:
a first receiver configured to receive a plurality of input medical texts tagged with potential medical codes;
a data curator configured to curate and validate the plurality of input medical texts, and to output a subset of medical texts that are validated and tagged with medical codes;
a classification model engine configured to use the subset of tagged and validated medical texts to model the associations between the medical texts and the medical codes, and to generate a medical text learning model based on the associations, wherein the associations between the medical texts and the medical codes for the tagged and validated medical texts are modelled using a Labelled Latent Dirichlet Allocation topic model, and wherein the medical text learning model uses a convolutional neural network;
an inputter configured to input a specimen text relating to a patient into the medical text learning model;
a specimen text processor configured to process the specimen text using the medical text learning model, and identify suggested medical codes based on the specimen text; and
an outputter configured to output diagnoses, symptoms and treatments linked to the suggested medical codes for assisting medical personnel in providing a diagnosis for the patient.

11. The method of claim 7, further comprising generating a single list of top matching medical standard code from the plurality of logical components.

12. The medical diagnostic aid of claim 10, further comprising:
a second receiver configured to receive an unstructured input;
an analyser and parser configured to split the unstructured input into a plurality of logical components, and to detect medical terms in the plurality of logical components;
a mapping engine configured to receive a medical classification hierarchy of medical standard codes in the form of a knowledge graph, and semantically annotate the knowledge graph with synonyms of medical terms used in the medical standard codes;
an automatic coding solver configured to analyse the medical terms detected in the plurality of logical components by the analyser and parser, to generate a list of potential matching medical standard codes for each of the medical terms, to compare the lists of potential matching medical standard codes, and to output top matching medical standard codes based on the comparison; and
an enrichment engine configured to enrich the unstructured input with the top matching medical standard codes, and to output the unstructured input tagged with the top matching medical standard codes as one of the plurality of input medical texts received by the first receiver.

13. The medical diagnostic aid of claim 12, wherein the automatic coding solver is further configured to generate a single list of top matching medical standard code from the plurality of logical components.

14. A computer readable medium comprising code which, when executed by a computer, causes the computer to execute the method of claim 1.

15. A diagnostic device, comprising:
initialization circuitry configured to
receive a plurality of input medical texts tagged with potential medical codes;
curate and validate the plurality of input medical texts to output a subset of medical texts that are validated and tagged with medical codes;
use the subset of tagged and validated medical texts to model the associations between the medical texts and the medical codes, and generate a medical text learning model based on the associations, wherein the associations between the medical texts and the medical codes for the tagged and validated medical texts are modelled using a Labelled Latent Dirichlet Allocation topic model, and wherein the medical text learning model uses a convolutional neural network; and
diagnostic circuitry configured to
receive a specimen text relating to a patient into the medical text learning model;
process the specimen text using the medical text learning model;

identify suggested medical codes based on the specimen text; and output diagnoses, symptoms and treatments linked to the suggested medical codes for assisting medical personnel in providing a diagnosis for the patient.

16. The diagnostic device of claim 15, further comprising:

tagging circuitry configured to split an unstructured input into a plurality of logical components, and to detect medical terms in the plurality of logical components;

receive a medical classification hierarchy of medical standard codes in the form of a knowledge graph, and semantically annotate the knowledge graph with synonyms of medical terms used in the medical standard codes;

analyse the medical terms detected in the plurality of logical components by the analyser and parser, to generate a list of potential matching medical standard codes for each of the medical terms, to compare the lists of potential matching medical standard codes, and to output top matching medical standard codes based on the comparison;

enrich the unstructured input with the top matching medical standard codes, and output the unstructured input tagged with the top matching medical standard codes as one of the plurality of input medical texts received by the initialization circuitry.

17. The diagnostic device of claim 16, wherein the tagging circuitry is further configured to generate a single list of top matching medical standard code from the plurality of logical components.

* * * * *